United States Patent [19]
Schildmeyer et al.

[11] Patent Number: 5,675,405
[45] Date of Patent: Oct. 7, 1997

[54] CONDENSATION NUCLEUS COUNTER EMPLOYING SUPERSATURATION BY THERMAL DIFFERENTIATION

[75] Inventors: Frederic C. Schildmeyer; Brian J. Shahan, both of Grants Pass, Oreg.

[73] Assignee: Met One, Inc., Grants Pass, Oreg.

[21] Appl. No.: 695,658

[22] Filed: Aug. 12, 1996

[51] Int. Cl.$^6$ ................................................. G01N 15/06
[52] U.S. Cl. ........................................ 356/37; 356/339
[58] Field of Search ................................ 356/37, 336, 338, 356/339

[56] References Cited

U.S. PATENT DOCUMENTS

| | | | |
|---|---|---|---|
| 4,449,816 | 5/1984 | Kohsaka et al. | 356/37 |
| 4,790,650 | 12/1988 | Keady | 356/37 |
| 4,950,073 | 8/1990 | Sommer | 356/37 |
| 5,026,155 | 6/1991 | Ockovic et al. | 356/37 |
| 5,118,959 | 6/1992 | Coldow | 356/37 |
| 5,239,356 | 8/1993 | Holländer et al. | 356/37 |

*Primary Examiner*—Richard A. Rosenberger
*Attorney, Agent, or Firm*—Thomas Schneck

[57] ABSTRACT

A condensation nucleus counter features an entropy control mechanism to regulate the entropy of a vaporized fluid present in a saturator, thereby facilitating supersaturation of the same about particulates entrained in a sample gas stream before the same passes through a condenser. The condensation nucleus counter includes a supply of sample gas, conduits adapted to allow the sample gas stream to flow therethrough, a saturator, a condenser and an optical detector, all of which are in fluid communication with each other. The manifold is disposed between the conduit and the saturator, and also a temperature control device. The manifold comprises a feed chamber and a plurality of channels positioned so that the sample gas stream entering the feed chambers evenly divides into a plurality of flows, with each flow entering the saturator. The temperature control device regulates the temperature difference between the flows entering the saturator and the vaporized fluid contained so as to be within a specified range. In this fashion, supersaturation occurs near the point where the sample flows enter the saturator.

18 Claims, 2 Drawing Sheets

CONDENSATION NUCLEUS COUNTER EMPLOYING SUPERSATURATION BY THERMAL DIFFERENTIATION

TECHNICAL FIELD

The present invention pertains to the field of airborne particle detection systems. Specifically, the present invention pertains to a condensation nucleus counter ideally suited for detecting particles of submicron size.

BACKGROUND ART

The behavior and characterization of very small particles, typically those having a diameter smaller than three micrometers, in gaseous media has become increasingly important as more is learned about the effects these particles have in differing environments. For example, as air pollutants, very small particles pose a significant health risk, because these particles are difficult to control by filtering. The health risk is exacerbated by the body's natural defenses being unable to prevent these particulates from being deposited in the lungs.

Also, very small particles have posed significant problems in manufacturing processes, especially microelectronic fabrication. Microelectronic fabrication requires a "clean room" in which particulate contaminants, e.g., dust, are typically filtered from an atmosphere of a room. Failure to provide a "clean room" results in particulate contamination of the devices which reduces yield. As mentioned above, however, very small particles are not easily controlled by filtering; thus, the filters used in "clean rooms" are usually inadequate to remove these particles from the atmosphere. Moreover, given the small size of these particles, most particle detectors lack the necessary resolution to detect their presence.

Condensation nucleus counters (CNCs) are well known particulate detectors that provide the resolution necessary to detect very small particles. CNCs operate on the principle of a cloud chamber. Liquid obtained by supersaturation of a gas condenses upon sub-micron particles entrained in the gas, producing micron-sized droplets. The humidified gas is passed through a cloud chamber where a fixed volume expansion produces condensation on the particles. In this fashion, the particles function as condensation nuclei. The cloud of droplets pass through a view volume of a particle counter operating according to light extinction principles. The droplets attenuate the light beam of the particle counter, resulting in an appropriate output signal relative to particle concentration. The resolution of CNCs is dependent upon the size of the droplets formed on the particles, which is a function of condensation time. The time for condensation to accumulate on the particle is a function of both the flow rate of the gas and the length of the flow path through the counter.

U.S. Pat. No. 5,239,356 to Hollander et al. discloses a condensation nucleus counter including a humidifier zone, a condensation zone extending orthogonally thereto and an optical detection system. The humidifying zone includes a duct and a hollow space extending parallel to the duct, but separated therefrom by a permeable material. A vaporizable liquid is received within the hollow space. The condensation zone includes a duct and a hollow space extending parallel thereto. Separating the duct from the hollow space is a permeable material. Particulate matter, entrained in sample air, is guided into the duct of the humidifying zone, where it is saturated. Upon passing through the condensation zone, the saturated air is supersaturated and condenses around the particulates.

U.S. Pat. No. 5,026,155 to Ockovic et al. discloses a process for sizing particles using condensation nucleus counting. The process employs a standard condensation nucleus counter in which the condensing temperature of a saturated working fluid is incrementally adjusted. In this manner, the sensitivity of the counter may be adjusted to afford discrimination of particles entrained in a gas, according to size.

U.S. Pat. No. 4,950,073 to Sommer discloses a submicron particle counter for counting particles entrained in air which includes a saturator, a condenser and an optical detector. Conduits extend through a bath of liquid contained in the saturator so that sample streams passing therethrough are heated by the bath. A flow divider separates the sample stream into a plurality of laminar flow streams, corresponding to the number of conduits in the bath. The condenser is a heat exchanger having a plurality of tubes with funnel-shaped inlet ends. The inlet ends are positioned over the bath of the saturator, with the tubes being inclined toward their inlet ends so that condensed vapor flows back into the bath.

U.S. Pat. No. 4,790,650 to Keady discloses a condensation nucleus counter including an inlet orifice leading to a flow path within a saturator. A condenser is in fluid communication with the saturator. Particulates entrained in a gas flow passing through the saturator have condensation accumulated thereon, forming a plurality of droplets. The plurality of droplets pass through an optical counter.

U.S. Pat. No. 4,449,816 to Kohsaka et al. discloses a system and a method of measuring hyperfine particles including a mixing chamber in fluid communication with both a saturated vapor chamber and a high temperature vapor chamber. An aerosol inlet is in constant fluid communication with the high temperature vapor chamber. The inlet is also in selective fluid communication with the saturated vapor chamber via a valve. An air aerosol containing fine particles is led into both the saturated vapor chamber and the high temperature vapor chamber, respectively, to produce saturated vapor aerosols. The two saturated vapor aerosols are led into the mixing chamber so that the aforementioned vapor is condensed on the aerosol particles. A particle detection station is included to measure the aerosol particles.

A drawback with the aforementioned condensation nucleus counters is that they are large and cumbersome, while providing limited resolution. What is needed is a condensation nucleus counter having improved resolution with increased flow rate and reduced size.

SUMMARY OF THE INVENTION

In accord with the present invention, a condensation nucleus counter features an entropy control mechanism which causes supersaturation of vapor in a saturator about particulate matter, entrained in a sample gas stream as the sample gas stream enters the saturator. In this fashion, super saturation conditions are achieved from the initial diffuse vapor state to facilitate heterogenous condensation. The vapor-diffusion-supersaturation process continues to contribute to a final thermal macrostate about the particulate nuclei as the sample gas passes through the saturator and enters the condenser. The condensation nucleus counter includes a supply of a sample gas, conduits adapted to allow the sample gas stream to flow therethrough, a saturator, a condenser and an optical detector, all of which are in fluid communication with each other. The saturator is disposed between the condenser and the conduit, with the condenser disposed between the detector and the saturator. In this manner, particles entrained in a sample gas pass through the conduit and enter the saturator. Upon exiting the saturator, the particles enter the condenser whereby the size of the droplets are normalized and enter the detector. The detector, operating according to either light extinction or light scattering principles, senses light intensity fluctuations corresponding to the presence of the droplets and produces an appropriate output signal identifying the same.

The entropy control mechanism includes a fluid distribution manifold disposed between the conduit and the saturator, as well as a temperature control device. The manifold comprises of a feed chamber and a plurality of channels extending from the feed chamber. The plurality of channels are of appropriate dimensions, and are positioned, so that the sample gas stream entering the feed chamber is evenly divided into a plurality of flows, with each of the flows entering into the saturator. The temperature control device regulates the temperature differential between the flows entering the saturator and the vaporized fluid, contained therein, to be within a specified range. In this fashion, initial supersaturation occurs proximate to the point in the saturator where the flows enter. The temperature control device typically includes a plurality of heating systems. One heating system is in thermal communication with the sample gas stream in the conduit to maintain the same at a constant temperature, above ambient room temperature. A second heating system is in thermal contact with the reservoir to maintain the temperature of the vapor contained therein within a predetermined range, warmer than the temperature of the sample gas stream. A third heating system is in thermal contact with the condenser to maintain the atmosphere within the condenser at a constant temperature, higher than the sample gas stream, but lower than the vaporizing fluid in the reservoir comprising the saturator.

BEST MODE FOR CARRYING OUT THE INVENTION

Figure 1:
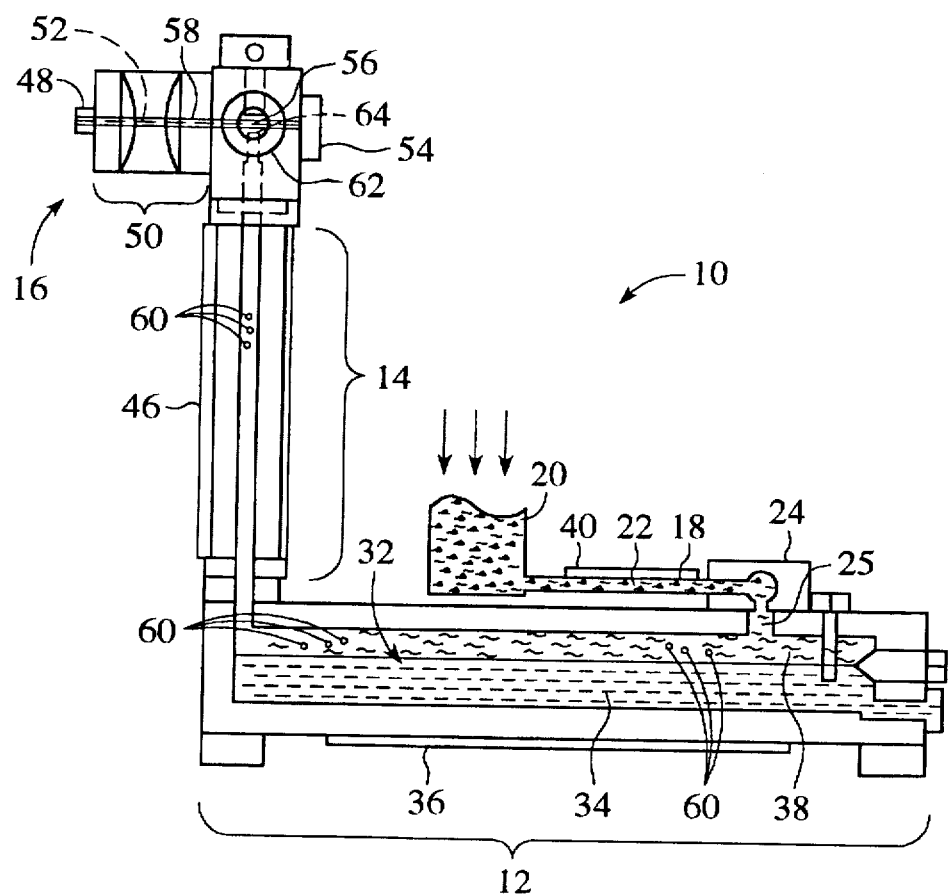
FIG. 1 is sectional side view of a condensation nucleus counter constructed in accord with the present invention.

With reference to FIG. 1, a condensation nucleus counter 10 includes a saturator 12, a condenser 14, an optical detector 16 and a conduit 18, all of which are in fluid communication with each other. Conduit 18 is coupled to a supply of a sample gas 20 and is adapted to allow a sample gas stream 22 to flow therethrough. Saturator 12 is disposed between condenser 14 and conduit 18, with condenser 14 disposed between detector 16 and saturator 12. A fluid distribution manifold 24 is disposed between conduit 18 and saturator 12, proximate to an inlet 25 of saturator 12.

Figure 2:
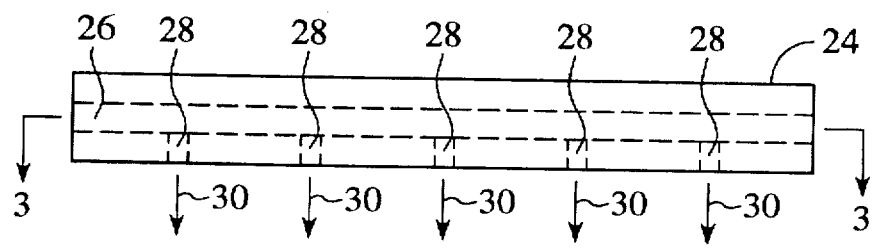
FIG. 2 is a bottom view of a fluid distribution manifold shown in FIG. 1.
Figure 3:
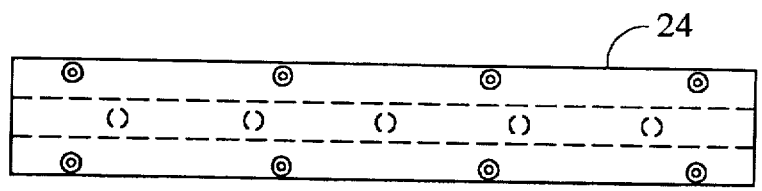
FIG. 3 is a bottom view of the fluid distribution manifold shown in FIG. 2, taken along lines 3—3.
Figure 4:
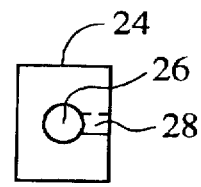
FIG. 4 is an end view of the fluid distribution manifold shown in FIG. 3.

Referring also to FIGS. 2–4, fluid distribution manifold 24 includes a feed chamber 26 and a plurality of channels 28 extending therefrom. Channels 28 are positioned so that sample gas stream 22 entering feed chamber 26 is evenly divided into a plurality of flows 30, with each flow 30 passing through inlet 25 and entering saturator 12.

Saturator 12 defines a saturation chamber 32 that contains a chemical species in a two phase state: liquid 34 and vapor 38. Liquid 34 maintains a reservoir from which the vapor 38 diffuses into the saturator space. Typically, the chemical species is referred to as a vaporizable fluid and comprises of alcohol, preferably glycerol. A first heating system 36 is in thermal contact with saturator 12 to produce the two phase fluid mixture in chamber 32. To ensure efficient thermal transfer between heating system 36 and fluid 34, it is preferred to form saturator from a metal, typically aluminum or an aluminum alloy. Heating system 36 is operated to maintain the temperature of vapor 38 within a predetermined range.

A second heating system 40 is in thermal contact with sample gas stream 22. Second heating system 40 maintains the temperature of flows 30 entering saturator 12 within a predetermined range, with the temperature of vapor 38 maintained above the temperature of flows 30. In this fashion, first 36 and second 40 heating systems function as a temperature control system to maintain a temperature differential between each flow 30, passing through inlet 25, and vapor 38. The aforementioned temperature differential is maintained within a range of 60° to 70° C.

Figure 5:
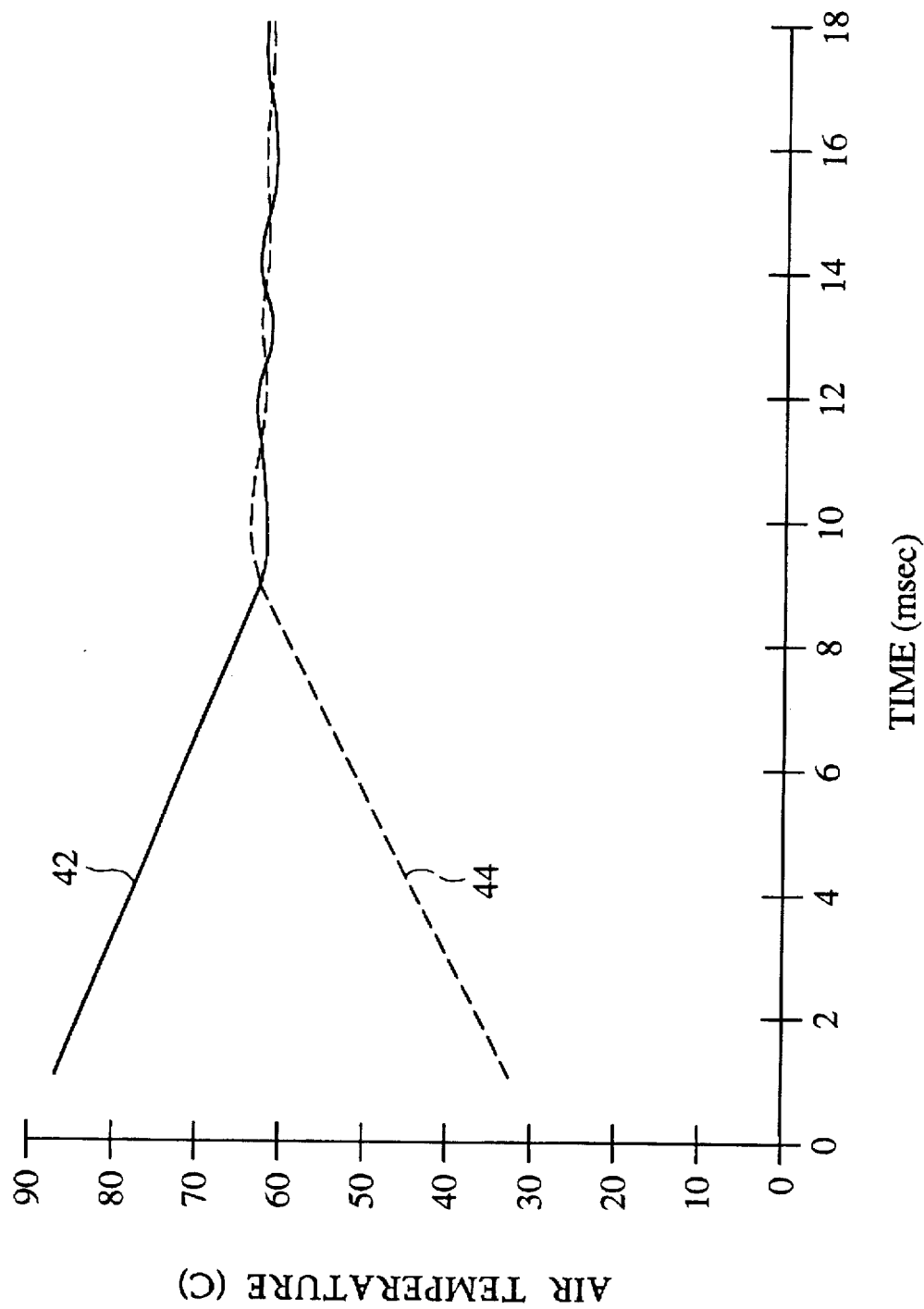
FIG. 5 is a graph showing the thermal transfer between the heated vapor contained in a saturator of the condensation nucleus counter, shown in FIG. 1, and a sample gas stream introduced into the saturator by a fluid distribution manifold shown in FIGS. 2–4.

Referring also to FIG. 5, it has been found that the temperature differential reduces the entropy associated with vapor 38, positioned proximate to inlet 25. The aforementioned temperature differential creates supersaturation conditions that initiate condensation to form about particulate matter present in flows 30, upon entering saturator 12. Specifically, both the positional and thermal disorder, present in vapor 38, diminishes by interaction with flows 30. The rapid cooling of vapor 38 by flows 30 causes supersaturation of the same. As shown by graphs 42 and 44, vapor 38, shown as a solid line, cools approximately 30° C. within 10 msec. Simultaneously, flows 30, shown as a dashed line, warms approximately 30° C. in the same time, thereby undergoing an increase in entropy. The transforming thermal states begin stabilizing through thin-film formation of vapor 38 onto the surfaces of particulate matter positioned proximate to inlet 25, thereby initiating condensation. By initiating droplet growth in saturator 12, the resolution of counter 10, for a given length of flow path, is greatly increased, because the droplet growth on particulate matter entering condenser 14 has already initiated. Thus, counter 10 affords a higher resolution counter for a given length of flow path and a given flow rate.

To stabilize and facilitate droplet growth, the atmosphere of condenser 14 is maintained at a temperature which is lower than the temperature of vapor 38. To that end, a third heating system 46 is in thermal communication with condenser 14. It is preferred that the temperature of the condenser 14's atmosphere is heated to exceed the temperature of sample gas stream 22 and, therefore, exceed the temperature of the ambient environment that surrounds counter 10. By heating condenser 14's atmosphere and the sample gas stream 22 to exceed the temperature of the environment surrounding counter 10, greater temperature stability is achieved. It was recognized that by employing only heating systems to induce and maintain heterogenous condensation, cooling techniques could be abrogated. Cooling techniques of the prior art lend themselves to support systems (liquid or air cooling), greater cost (component complexity) and reliability problems (thermoelectric cooler failure) which exacerbates problems with controlling the size of droplets produced. By heating condenser 14's atmosphere, the droplet size grown may be effectively controlled, as discussed below.

Typically, detector 16 includes a light source 48 optically coupled to a lens assembly 50, which defines an optical axis 52. Disposed coaxially on optical axis 52, opposite to light source 48, is a light trap 54. Lying along optical axis 52, between light source 48 and light trap 54, is a view volume 56. Light source 48 directs a beam 58 along optical axis 52 through view volume 56. Droplets 60 present therein cause a portion of beam 58 to scatter from optical axis 52, which is collected by a detector 62. Detector 62 produces electrical signals corresponding to the light detected, which may be digitized and displayed accordingly.

In operation, sample gas stream 22 travels through conduit 18 from supply 22 entering feed chamber 26 of fluid distribution manifold 24. Manifold 24 evenly divides sample gas stream 22 by maintaining a pressure drop gradient through channels 28 forming a plurality of flows 30. Flows 30 enter saturator 12, at approximately identical velocities, through inlet 25. Second heating system 40 increases the temperature of sample gas stream 22 so that the temperature of flows 30 are maintained at a constant temperature of approximately. 32° C.±2° C. First heating system 36 maintains the temperature of vapor 38 in saturation chamber 32 between 90°–100° C. Upon flows 30 entering saturator 12, heterogeneous nucleation occurs proximate to inlet 25, with particulates present in flows 30 forming nuclei around which condensation of the gas vapor mixture occurs. Droplets 60 formed from the heterogenous nucleation travel through vapor 38 toward condenser 14, where further growth occurs due to molecular collisions with other vapor molecules from saturation chamber 32.

Droplets 60 move through vapor 38 onto condenser 14. Upon exiting saturator 12, however, droplets have differing sizes due to the supersaturation process. More particularly, as growth in saturator 12 occurs, in part, from molecular collisions, the diffusion rate and collision state are not uniform for all droplets. This results in the final droplet diameter probability convoluting with the thermal state distribution function to form a spread in final droplet diameters. Condenser 14 provides some element of control of the final thermal state distribution and narrows the droplet diameter distribution through evaporation and condensation processes. Specifically, heating system 46 raises condenser 14's atmosphere to a temperature in the range of 55° to 65° C. so that droplets 60 having condensed to a larger spectrum of diameters undergo partial evaporation. Droplets associated with a smaller diameter spectrum continue condensation growth. This process of droplet diameter normalization is dependent on tuning the condenser temperature to the mean temperature of the droplet spectrum that leaves saturator 12. To that end, the temperature of condenser 14's atmosphere is maintained at a temperature in excess of the temperature of the environment in which counter 10 is disposed, thereby facilitating a droplet growth using a heat only control system.

Finally, condenser 14 is a parallel plate design with substantially smooth inner surfaces. The smooth surfaces frustrate formation of large condensation droplets on the inner walls and allows drainage back to saturator 12. This helps avoid false counts, i.e., detection of droplets not formed around particulates, which increases the reliability of counter 10 by ensuring only particulate matter of interest is present in detector 16. False counts may be further reduced by having a heated nozzle 64 disposed so as to place condenser 14 in fluid communication with view volume 56. Preferably, nozzle 64 is heated to a temperature approximately ten degrees cooler than saturator 12. The efficiency is further increased by providing all droplets 60 with substantially the same diameter growth so that particulate matter of interest will be provided with a sufficient cross-section to be sensed by detector 16 when passing through view volume 56.

We claim:

1. A condensation nucleus counter for detecting particles entrained in a sample gas stream, said counter comprising:

a conduit adapted to allow said sample gas stream to flow therethrough;

a saturator having an inlet in fluid communication with said conduit, said saturator containing a vaporized fluid;

a condenser in fluid communication with said saturator;

means, in thermal contact with said sample gas stream, for decreasing entropy associated with vaporized fluid positioned proximate to said inlet to produce supersaturation; and a detector in data communication with said sample gas stream.

2. The condensation nucleus counter as recited in claim 1 wherein said decreasing means includes a fluid distribution manifold disposed between said conduit and said inlet, said manifold evenly dividing said sample gas stream into a plurality of flows so that each of said flows enter said inlet.

3. The condensation nucleus counter as recited in claim 1 wherein said decreasing means includes a first heating means for maintaining a temperature differential between said sample gas stream entering said saturator and said vaporized fluid.

4. The condensation nucleus counter of claim 3 wherein said temperature differential is in the range of 60° to 70° C.

5. The condensation nucleus counter as recited in claim 1 wherein said condenser has an atmosphere and further including a second heating means, in thermal contact with said condenser, for increasing a temperature of said atmosphere to exceed a temperature of said sample gas stream passing through said conduit.

6. The condensation nucleus counter as recited in claim 1 wherein said decreasing means includes a first means for heating said vaporized fluid to a first temperature and a second means for heating said sample gas stream to a second temperature, less than said first temperature, with a difference between said first and second temperatures, causing condensation to form on said particulate matter present in said gas stream positioned proximate to said inlet.

7. The condensation nucleus counter as recited in claim 1 wherein said vaporized fluid comprises of glycerol.

8. A condensation nucleus counter for detecting particles entrained in a sample gas stream, said counter comprising:

a conduit adapted to allow said sample gas stream to flow therethrough;

a saturator having an inlet in fluid communication with said conduit, said saturator containing a vaporized fluid;

a condenser in fluid communication with said saturator;

means, in thermal contact with said sample gas stream, for supersaturating vaporized fluid positioned proximate to said inlet;

a detector in data communication with said sample gas stream; and a condenser disposed between said detector and said saturator.

9. The condensation nucleus counter as recited in claim 8 wherein said supersaturating means includes a fluid distribution manifold disposed between said conduit and said inlet, said manifold having a feed chamber and a plurality of channels extending from said feed chamber, with said plurality of channels positioned with respect to said feed chamber to evenly divide said sample gas stream into a plurality of flows, with each of said flows entering said inlet.

10. The condensation nucleus counter as recited in claim 9 wherein said supersaturating means includes a first heating means for maintaining a constant temperature differential between said sample gas stream entering said saturator and said vaporized fluid.

11. The condensation nucleus counter as recited in claim 10 wherein said condenser has an atmosphere and further including a second heating means, in thermal contact with said condenser, for increasing a temperature of said atmosphere to exceed a temperature of said sample gas stream passing through said conduit.

12. The condensation nucleus counter as recited in claim 10 wherein said supersaturating means includes a first means for heating said sample gas stream to a first temperature and said vaporized fluid to a second temperature, greater than said first temperature, with a difference between said first and second temperatures causing condensation to form on said particulate matter present in said gas stream positioned proximate to said inlet.

13. The condensation nucleus counter as recited in claim 12 wherein said vaporized fluid is glycerol.

14. A method of measuring particulate matter entrained within a sample gas stream, comprising the steps of:

heating said sample gas stream to a first temperature;

providing a saturator containing a vaporizable fluid;

heating said vaporizable fluid to produce a vapor having a second temperature;

introducing said gas stream into said vapor, with a difference between said first and second temperatures creating a thermal differential causing said vapor to condense about said particulate matter to form a plurality of droplets;

providing a condenser having an atmosphere;

heating said atmosphere to a third temperature;

introducing said plurality of droplets into said atmosphere, whereby each of said plurality of droplets passing through said atmosphere obtain a predetermined diameter through condensation and evaporation processes; and measuring a physical attribute of said plurality of droplets exiting said condenser.

15. The method as recited in claim 14 wherein said third temperature is greater than said first temperature, but less than said second temperature.

16. The method as recited in claim 15 wherein said first temperature is greater than an ambient temperature.

17. The method as recited in claim 15 wherein said condenser atmosphere is heated in excess of 30° C.

18. The method as recited in claim 14 wherein said thermal differential is in the range of 60° C. to 70° C.

* * * * *